(12) United States Patent
Old et al.

(10) Patent No.: US 7,705,008 B2
(45) Date of Patent: Apr. 27, 2010

(54) PROSTAGLANDIN ANALOGS

(75) Inventors: David W. Old, Irvine, CA (US); Danny T. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/191,779

(22) Filed: Aug. 14, 2008

(65) Prior Publication Data

US 2009/0069309 A1      Mar. 12, 2009

Related U.S. Application Data

(63) Continuation of application No. 10/552,083, filed as application No. PCT/US2005/019409 on Jun. 2, 2005, now Pat. No. 7,427,614.

(60) Provisional application No. 60/584,962, filed on Jul. 2, 2004, provisional application No. 60/600,165, filed on Aug. 9, 2004.

(51) Int. Cl.
| | |
|---|---|
| C07D 265/10 | (2006.01) |
| C07D 279/06 | (2006.01) |
| C07D 239/10 | (2006.01) |
| A61K 31/54 | (2006.01) |
| A61K 31/513 | (2006.01) |
| A61K 31/535 | (2006.01) |

(52) U.S. Cl. .................. 514/269; 544/315; 544/316; 544/318

(58) Field of Classification Search ............ 544/315, 544/316, 318; 514/269
See application file for complete search history.

(56) References Cited

U.S. PATENT DOCUMENTS

2004/0142969 A1    7/2004  Elworthy

FOREIGN PATENT DOCUMENTS

| WO | WO2004/063158 A1 | 7/2004 |
| WO | WO2004/085430 A1 | 10/2004 |

OTHER PUBLICATIONS

Wolff Manfred E. "Burger's Medicinal Chemistry, 5ed, Part 1" John Wiley & Sons, 1995, pp. 975-977.*
Banker, G.S. et al, "Modern Pharmaceutices, 3ed." Marcel Dekker, New York, 1996, pp. 451 and 596.*

* cited by examiner

*Primary Examiner*—Kahsay T Habte
(74) *Attorney, Agent, or Firm*—Kevin J. Forrestal; John E. Wurst; Allergan, Inc.

(57) ABSTRACT

Compounds comprising

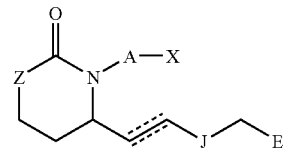

or a pharmaceutically acceptable salt or a prodrug thereof is disclosed herein. A, X, J, E, and Z are as described herein. These compounds are useful for treating diseases.

14 Claims, 5 Drawing Sheets

PROSTAGLANDIN ANALOGS

CROSS REFERENCE TO RELATED APPLICATIONS

Related Application

Figure 1:
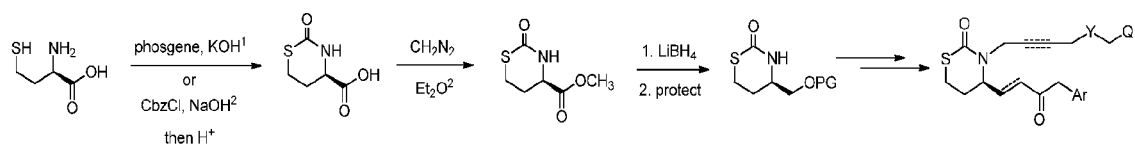

This application is a continuation application which claims the benefit of U.S. patent application Ser. No. 10/552,083, filed Oct. 4, 2005, which claims the benefit PCT application PCT/US2005/019409, filed on Jun. 2, 2005, which claims the benefit of Provisional Application Nos. 60/584,962, filed on Jul. 2, 2004 and 60/600,165, filed Aug. 9, 2004 which are hereby incorporated by reference in their entirety.

FIELD OF THE INVENTION

This invention relates to compounds which are useful as therapeutic agents. Among other potential uses, these compounds are believed to have properties which are characteristic of prostaglandins.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical β-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

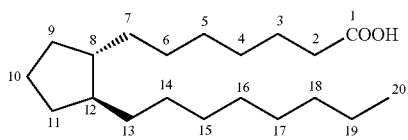

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins were earlier regarded as potent ocular hypertensives, however, evidence accumulated in the last two decades shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., *Invest. Opthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Opthalmol.* 105, 1036 (1987), and Siebold et al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of United States patents assigned to Allergan, Inc. prostaglandin esters with increased ocular hypotensive activity accompanied with no or substantially reduced side-effects are disclosed. Some representative examples are U.S. Pat. No. 5,446,041, U.S. Pat. No. 4,994,274, U.S. Pat. No.

5,028,624 and U.S. Pat. No. 5,034,413 all of which are hereby expressly incorporated by reference.

BRIEF DESCRIPTION OF THE INVENTION

A compound comprising

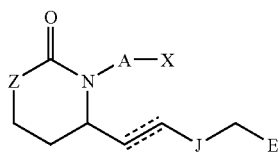

or a pharmaceutically acceptable salt or a prodrug thereof, is disclosed herein;

wherein a dashed line represents the presence or absence of a double bond or a triple bond;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O;

Z is O, S, or NR;

X is selected from the group consisting of $CO_2H$, $CONHR_2$, $CONR_2$, $CON(OR)R$, $CON(CH_2CH_2OH)_2$, $CONH(CH_2CH_2OH)$, $CH_2OH$, $P(O)(OH)_2$, $CONHSO_2R$, $SO_2NR_2$, $SO_2NHR$, and

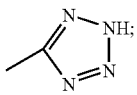

J is C=O or CHOH;

R is independently H, $C_1$-$C_6$ alkyl, phenyl, or biphenyl; and

E is $C_3$-$C_6$ alkyl, $C_4$-$C_{10}$ cycloalkyl, phenyl or napthyl having from 0 to 2 substituents, or a heteroaromatic moiety having from 0 to 2 substituents, wherein said substituents comprise up to 4 non-hydrogen atoms.

Methods of treating certain conditions or diseases, and compositions and medicaments related thereto are also contemplated.

BRIEF DESCRIPTION OF THE DRAWING FIGURES

FIGS. 1-5 illustrate methods of preparing the compounds disclosed herein.

DETAILED DESCRIPTION OF THE INVENTION

While not intending to limit the scope of the invention in any way, compounds having the stereochemistry indicated in the structure below may be particularly useful.

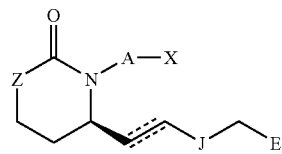

Pharmaceutically acceptable salts or prodrugs of compounds of the structure above are also considered to be particularly useful A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

In relation to the identity of A disclosed in the chemical structures presented herein, in the broadest sense, A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O. In other words, A may be —$(CH_2)_6$—, cis —$CH_2CH$=$CH$—$(CH_2)_3$—, —$CH_2C$≡$C$—$(CH_2)_3$—, or A may be a group which is related to one of these three moieties in that any carbon is substituted with S or O. For example, while not intending to limit the scope of the invention in any way, A may be an S substituted moiety such as one of the following or the like.

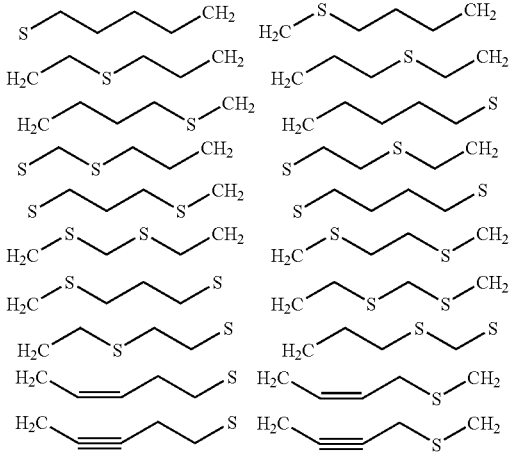

Alternatively, while not intending to limit the scope of the invention in any way, A may be an O substituted moiety such as one of the following or the like.

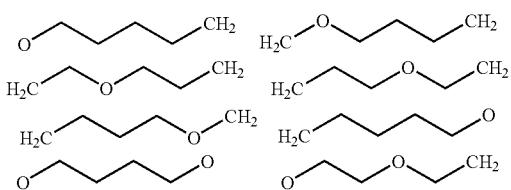

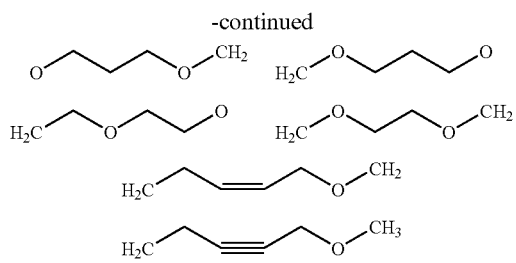

In certain compounds A is —(CH$_2$)$_4$OCH$_2$—, —CH$_2$CH=CHCH$_2$OCH$_2$—, or —CH$_2$C≡CCH$_2$OCH$_2$—, that is they can be generically described by the structure shown below.

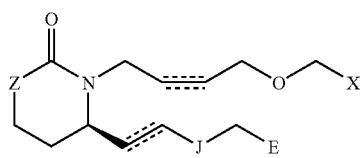

Pharmaceutically acceptable salts and prodrugs thereof are also contemplated.

In other embodiments, A is —(CH$_2$)$_6$—, cis —CH$_2$CH=CH—(CH$_2$)$_3$—, or —CH$_2$C≡C—(CH$_2$)$_3$— having no heteroatom substitution, that is they can be generically described by the structure shown below.

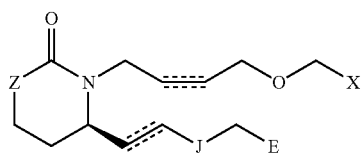

Pharmaceutically acceptable salts and prodrugs thereof are also contemplated.

While not intending to limit the scope of the invention in any way, compounds according to the structures below are specifically contemplated.

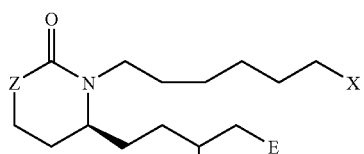

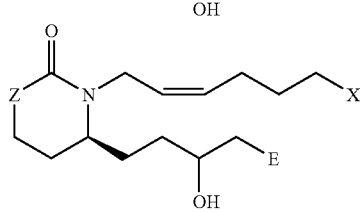

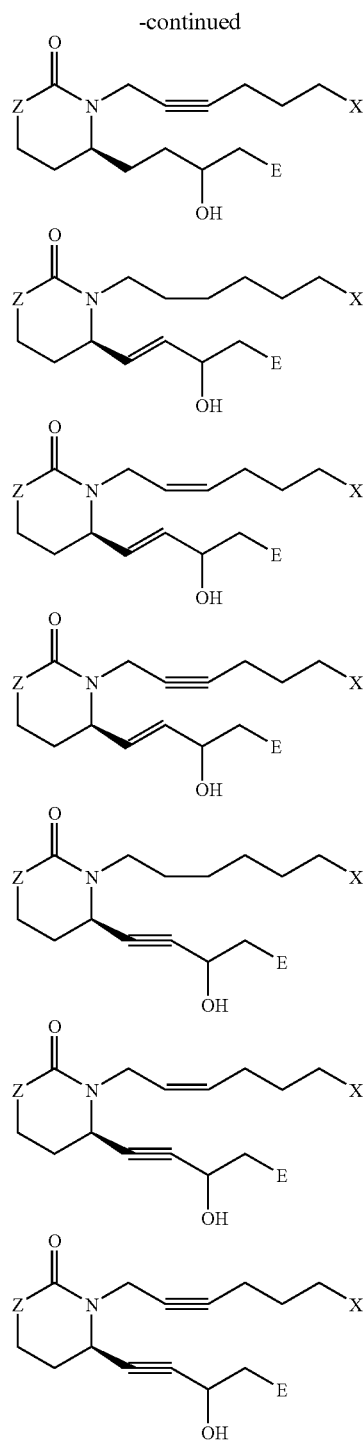

Pharmaceutically acceptable salts or prodrugs of compounds of these structures are also contemplated.

E can vary broadly, as E may be $C_3$-$C_6$ alkyl, $C_4$-$C_{10}$ cycloalkyl, phenyl or napthyl having from 0 to 2 substituents, or a heteroaromatic moiety having from 0 to 2 substituents, wherein said substituents comprise up to 4 non-hydrogen atoms.

Thus, E may be $C_3$-$C_6$ alkyl, including linear alkyl such as n-propyl, n-butyl, n-penyl, or n-hexyl; branched alkyl such as iso-propyl, iso-butyl and other branched butyl isomers, isopentyl and other branched pentyl isomers, and the branched hexyl isomers. E may also be $C_4$-$C_{10}$ cycloalkyl, including cyclobutyl, cyclopentyl, cyclohexyl, cycloheptyl, cyclooctyl, cyclononyl, and cyclodecyl; cycloalkyl with linear or branched substituents are also considered cycloalkyl such as methylcyclohexyl, methylcyclobutyl, ethylcyclohexyl and the like. A cycloalkyl ring may also be attached the remainder of the molecule via a linear or branched alkyl fragment, such as for example, the following moieties

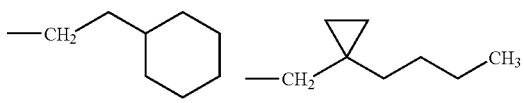

and the attaching fragment as well as the cyclic part is considered to be the entire cycloalkyl moiety. Additionally, any other hydrocarbon moiety which can be conceived by a person of ordinary skill in the art which consists of a cycloalkyl ring in any form with any other combination of linear or branched alkyl groups is a cycloalkyl moiety.

E may also be phenyl or naphthyl having from 0 to 2 substituents.

E may also be a heteroaromatic moiety having from 0 to 2 substituents.

The substituents comprise up to 4 non-hydrogen atoms, in other words, there are from 1 to 4 atoms which are not hydrogen, and any number of hydrogen atoms required to form the complete substituent. For example, a methyl substituent has 1 carbon atom and 3 hydrogen atoms. Other example substituents include hydrocarbon moieties comprising from 1 to 4 carbon atoms including alkyl such as ethyl, propyl, isopropyl, and butyl and isomers thereof; cyclic and unsaturated hydrocarbons having from 2 to 4 carbon atoms such as ethylenyl, propenyl, propynyl, cyclopropyl, cyclobutyl, etc; $CO_2H$ and salts thereof; alkoxy up to $C_3$ such as methoxy, ethoxy, propoxy, isopropoxy, and the like; carboxylic acid esters; CN; $NO_2$; halo, and halogen containing substituents such as $CF_3$, F, Cl, Br, and I; sulfonyl esters; $SO_3H$ and salts thereof; and the like. Thus, for example, E may be phenyl, a naphthyl, or a heteroaromatic moiety such as thienyl, furyl, pyridinyl, benzothienyl, benzofuryl, and the like, having no substituents. Alternatively the aromatic or heteroaromatic moiety may be monoalkylsubstituted moiety such as methylphenyl, ethylbenzofuryl, propylthienyl, etc.; a monohalosubstituted moiety such as fluorophenyl, chlorofuryl, bromopyridinyl, etc.; or a monosubstituted aromatic moiety with another substituent having less than 4 non-hydrogen atoms. The aromatic or heteroaromatic moiety may also be a disubstituted moeity having the same or different substituents. These substituents may be in any reasonable position on the phenyl or naphthyl moiety.

While not intending to limit the scope of the invention in any way, compounds comprising

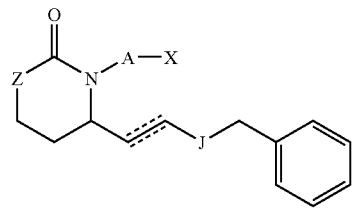

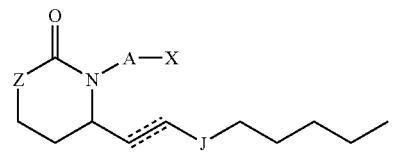

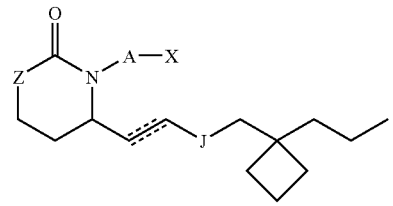

or pharmaceutically acceptable salts, or prodrugs thereof, are useful for the purposes disclosed herein.

While not intending to limit the scope of the invention in any way, in certain embodiments Z is O, such as in the examples below.

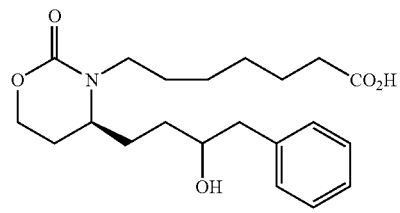

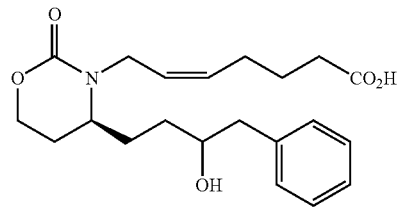

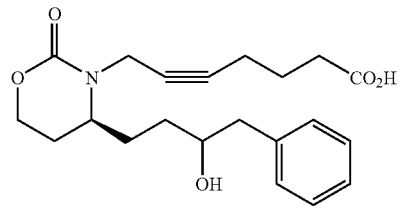

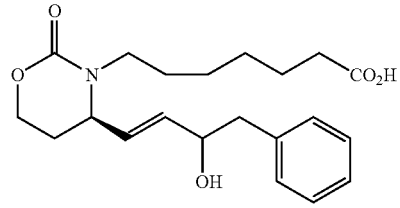

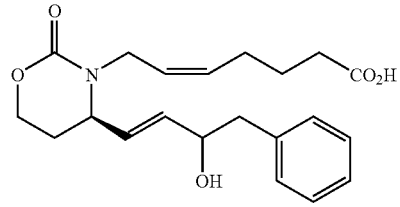

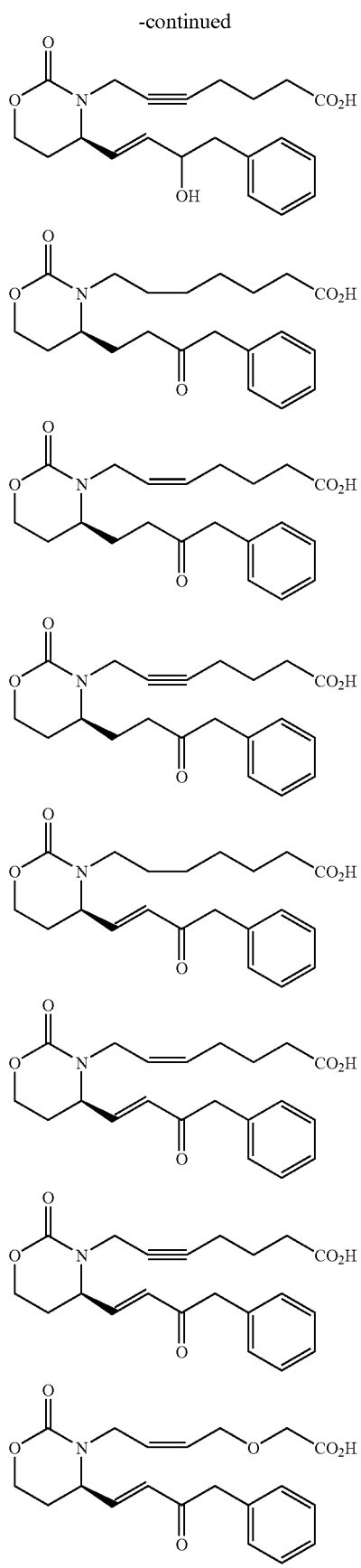
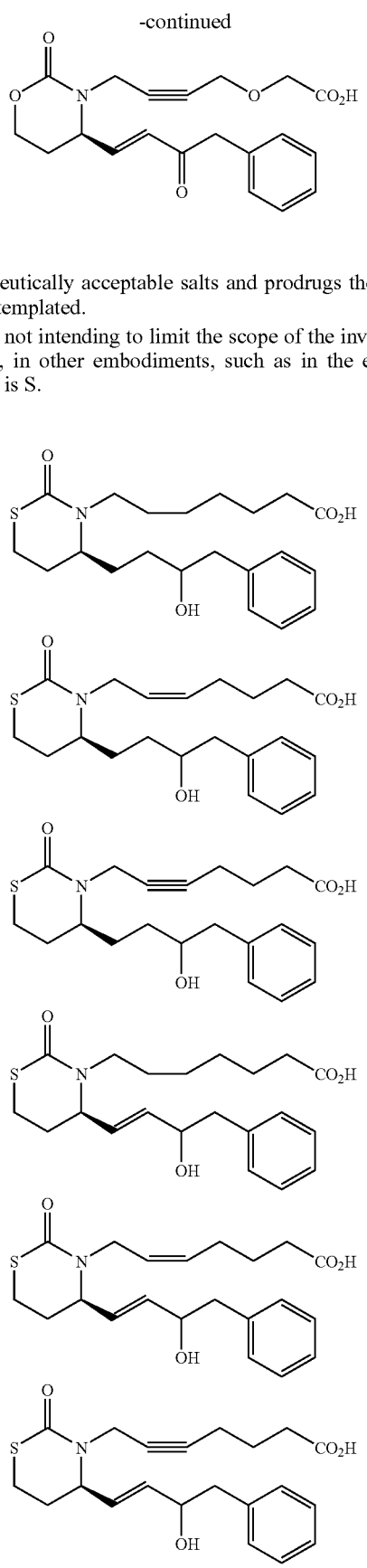
Pharmaceutically acceptable salts and prodrugs thereof are also contemplated.
While not intending to limit the scope of the invention in any way, in other embodiments, such as in the examples below, Z is S.

-continued

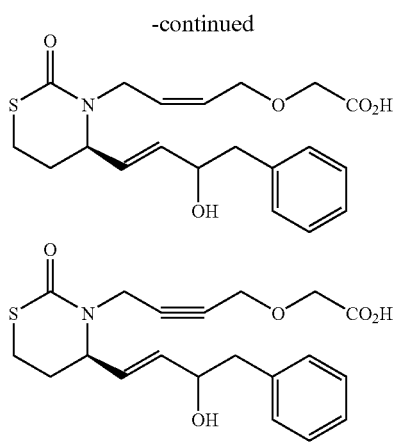

Pharmaceutically acceptable salts and prodrugs thereof are also contemplated.

While not intending to limit the scope of the invention in any way, in certain embodiments Z is NH, such as in the examples below.

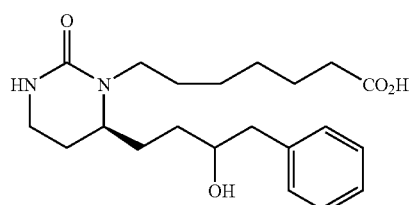

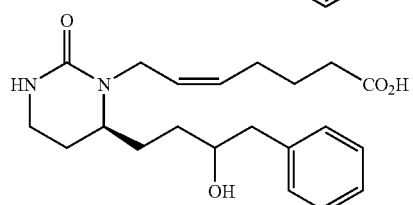

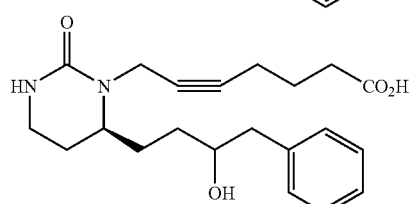

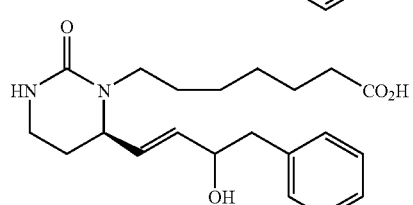

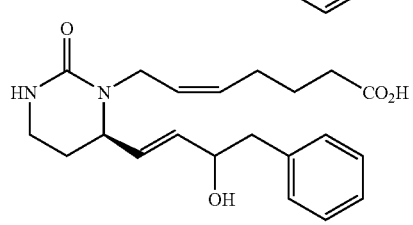

-continued

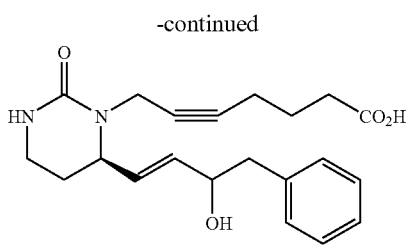

Pharmaceutically acceptable salts and prodrugs thereof are also contemplated.

While not intending to limit the scope of the invention in any way, in certain embodiments Z is NR, such as in the examples below.

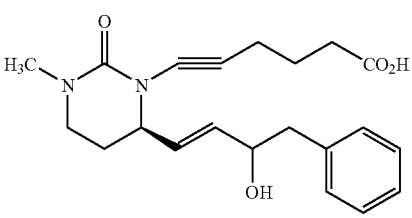

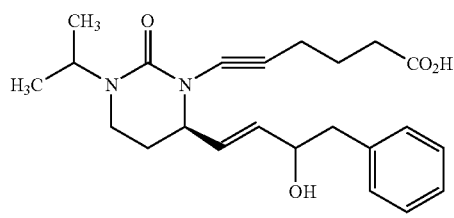

Pharmaceutically acceptable salts and prodrugs thereof are also contemplated.

J is C=O or CHOH, meaning that the following types of compounds, or pharmaceutically acceptable salts or prodrugs thereof, are contemplated.

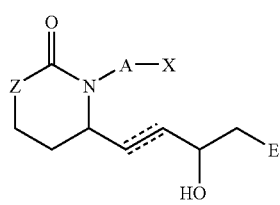

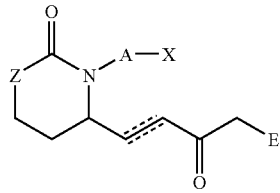

In other compounds, X is CO$_2$H, as depicted in the structure below.

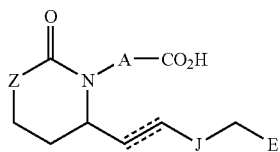

Pharmaceutically acceptable salts and prodrugs of compounds represented by the structure above are also contemplated.

Thus, while not intending to limit the scope of the invention in any way, the compounds shown below, and pharmaceutically acceptable salts and prodrugs thereof, are of interest.

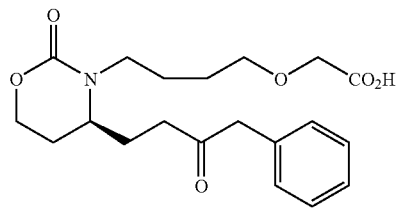
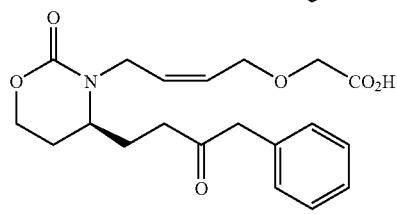
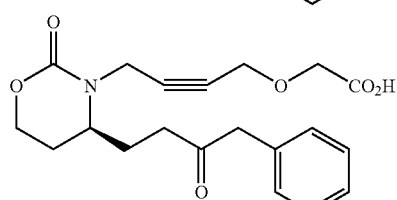
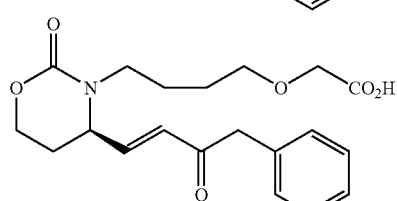
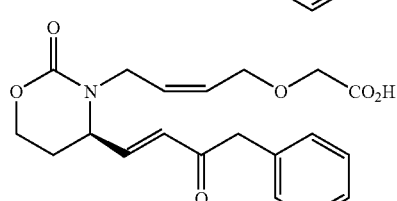
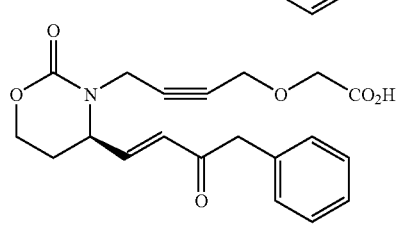

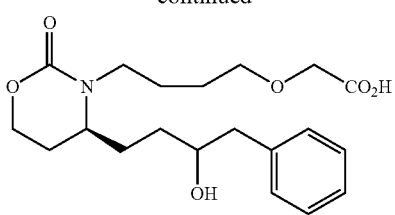
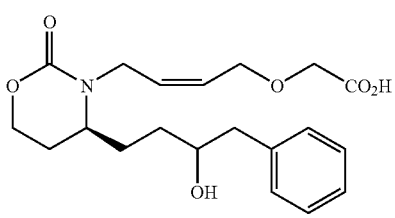
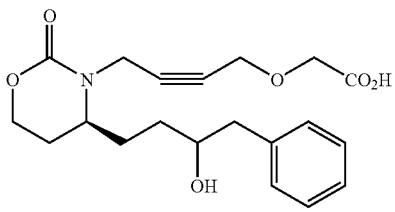
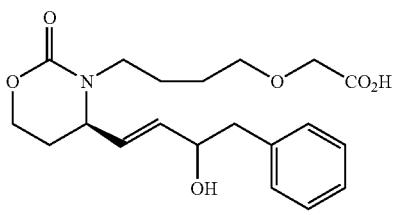
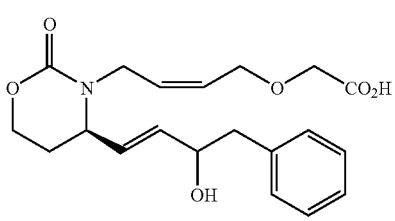
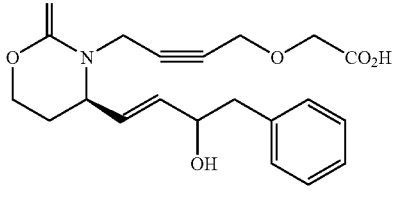

For compounds characterized by the phrases "X is $CO_2H$", "Z is NH", or the like, where the group could be converted to a pharmaceutically acceptable salt, or where a derivative of the group would make the compound a prodrug, a term for a group such as "$CO_2H$" or "NH" is intended to mean the actual group, the pharmaceutically salts, or the derivatives of the group which make the compound a prodrug.

While not intending to limit the scope of the invention in any way, other compounds of particular interest herein are those of the structures shown below, and pharmaceutically acceptable salts and prodrugs thereof.

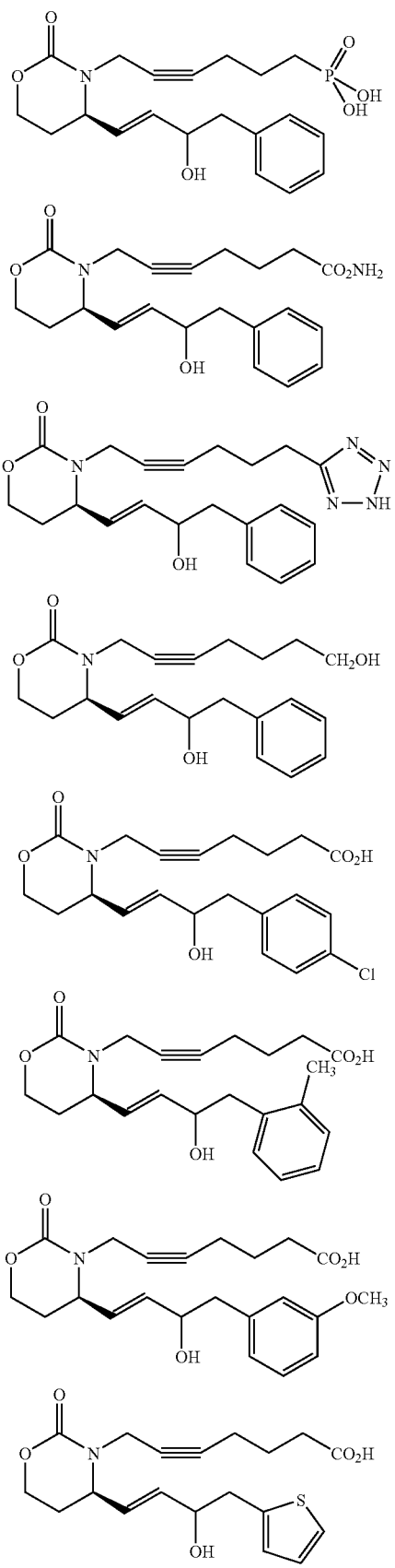

-continued

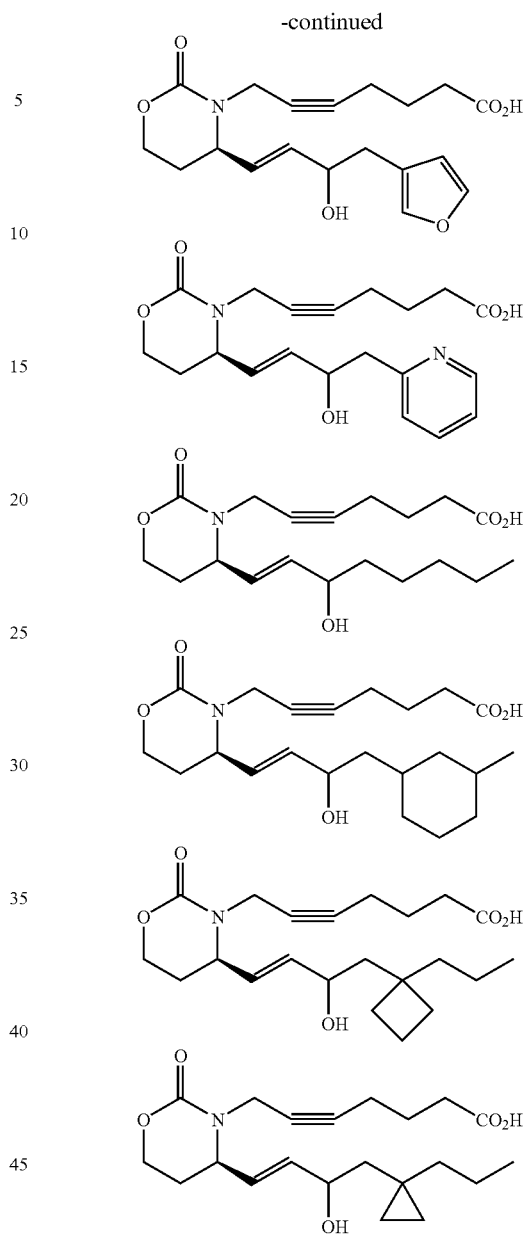

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

While not intending to limit the scope of the invention in any way, examples of prodrugs of the useful compounds disclosed herein include those shown below.

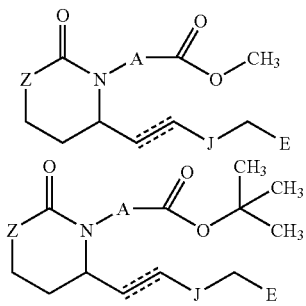

The tetrazole group,

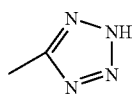

has two tautomeric forms, which can rapidly interconvert in aqueous or biological media, and are thus equivalent to one another. The tautomer of the tetrazole shown above is shown below.

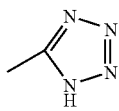

For the purposes disclosed herein, all tautomeric forms should be considered equivalent in every way.

The compounds disclosed herein are useful for the prevention or treatment of glaucoma or ocular hypertension in mammals, or for the manufacture of a medicament for the treatment of glaucoma or ocular hypertension.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid composition which is formulated for topical ophthalmic use is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Example 1

Compounds are prepared according to the following or analogous procedures.

Preparation of the [1,3]oxazinan-2-one or the [1,3]thiazinan-2-one structure such as that shown in Scheme 1 may be accomplished according to a number of published procedures.

For the [1,3]thiazinan-2-one structure, Pohl et al. (*Molecular Pharmacology* 1984, 25, 318-321) discloses a method for the preparation of "perhydro-2-oxo-1,3-thiazine-4-carboxylic acid" (POTZ) which was described therein as follows (see FIG. 1):

"Homocysteine (1 g, 7.4 mmol) was dissolved in 83 ml of water, and the solution was made basic with 8.3 ml of an aqueous solution of 40% potassium hydroxide. The mixture was cooled to approximately −5° (ice-salt bath) in an atmosphere of nitrogen and phosgene (1.17 g, 13.4 mmol, dissolved in 5 ml of toluene) was added dropwise over a period of 3 min, with vigorous stirring. After 30 min, concentrated hydrochloric acid was added to adjust the pH from approximately pH 10 to pH 7.5. The reaction mixture was washed with ethyl acetate (300 mL, two times) and made acidic to pH 2 with concentrated hydrochloric acid. It was then extracted with ethyl acetate (300 ml, four times) and the extracts were combined and dried over anhydrous magnesium sulfate. The dried organic extract was filtered by gravity, and the ethyl acetate was removed by rotary evaporation under vacuum to give 460 mg of a white solid. The product was crystallized from water to yield 157 mg (13% yield) of a pale white crystalline solid, m.p. 182-183° (uncorrected), which was characterized as POTZ from its chemical analysis, EIMS, and 13C-NMR spectrum."

Similarly, Cox and Wang (*J. Chem. Soc., Perkin Trans.* 1, 2001, 2022-2034) described a synthesis of the same compound, albeit under different conditions (see also FIG. 1):

" . . . treatment of homocysteine . . . with CbzCl under standard Schotten-Bauman conditions . . . after acidification and treatment with diethyl ether-diazomethane only the cyclic thiocarbamate was isolated."

The compounds disclosed herein are then prepared from this compound using the methods disclosed in U.S. Pat. No. 6,747,047 and United States Patent Application entitled "Piperidinyl Prostaglandin E Analogs", Filed Jun. 3, 2004, in the name of inventors David W. Old and Danny T. Dinh (hereafter referred to as the Old Application) which has not yet received a serial number.

Figure 2:
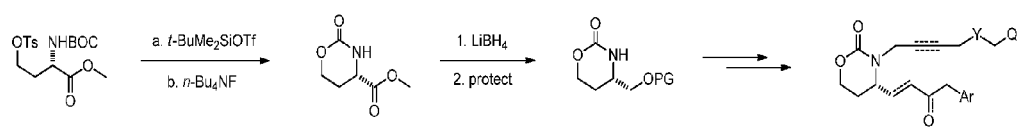

For the synthesis of the [1,3]oxazinan-2-one core structure, as indicated in FIG. 2, one might use the method of Sakaitani and Ohfune (*J. Am. Chem. Soc.* 1990, 12, 1150-1158) which discloses the following:

"To a stirred solution of 1 [tosylate] (149 mg, 0.38 mmol) and 2,6-lutidine (88 μL, 0.76 mmol) in dry $CH_2Cl_2$ (1 mL) at room temperature was added dropwise tert-butyldimethylsilyl trifluoromethanesulfonate (t-BuMe$_2$SiOTf; 131 μL, 0.57 mmol). The reaction mixture was stirred for 15 min, quenched with saturated aqueous ammonium chloride solution, and extracted with ether several times. The combined organic phase was washed with $H_2O$ and brine, dried (MgSO$_4$), and concentrated in vacuo to give N-(tert-butyldimethylsiloxycarbonyl)-O-(p-tolylsulfonyl)-L-homoserine methyl ester . . . the resulting silyl carbamate was treated with 380 μL, [1 M solution in tetrahydrofuran (THF), 0.38 mmol] of tetrabutylammonium fluoride in THF (2 mL) at 0° C. for 1 h and quenched with saturated aqueous ammonium chloride solution. The mixture was extracted with ethyl acetate several times. The combined organic phase was washed with $H_2O$ and then brine, dried ($MgSO_4$), and concentrated in vacuo to give the crude product, with upon purification by column chromatography on silica gel (elution with 50% EtOAc in ether) gave 5 [4-methoxycarbonyl)tetrahydro-1,3-oxazin-2-one]."

In this case, the antipode of the desired core is formed and the synthesis of the precursors of compounds disclosed herein would therefore require the amino acid derived from D-homoserine. The compounds disclosed herein are then prepared from the precursors using the Old methods.

Figure 3:
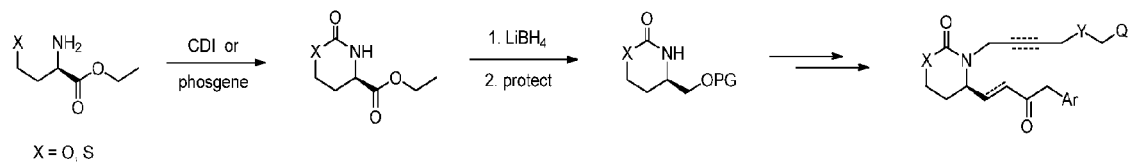

Alternatively, the synthesis of these six-membered cyclic carbamates and thiocarbamates, according to FIG. 3, could be based on analogy to the 5-membered ring core structures [Kubodera et al. (see *Heterocycles* 1982, 18, 259-263) and also Han et al. (see WO 2004/019938)]. In these cases the requisite amino acid serine or cysteine is cyclized using phosgene or carbonyl diimidazole (CDI) to form the desired core structure. In the case of the compounds disclosed herein, homoserine ethyl ester and homocysteine ethyl ester would be cyclized to the requisite core. Again the desired target molecules would be prepared using the Old methods.

Preparation of the tetrahydro-pyrimidin-2-one structure such as that shown in Scheme 4 may be accomplished according to a number of published procedures. The method of Billiot and Young (WO 03/103664) relies upon the Hoffmann rearrangement of a protected asparagine starting material to afford a desired imidazolidin-2-one core. Analogously, a protected glutamine starting material would afford the desired tetrahydro-pyrimidin-2-one core. From this core structure, the methods of the Billiot and Young PCT above or the methods of Saijo et al. (*Chem. Pharm. Bull.* 1980, 28(5), 1459-1467) would be used to elaborate the core molecule to the desired compounds. The migration of the Cbz protecting group from N-3 to N-1 is anticipated to occur by analogy to the Saito precedent. If this migration fails to occur, N-1 would be protected (either with BOC or a substituted benzyl group) prior to Cbz removal and N-3 alkylation.

Figure 5:
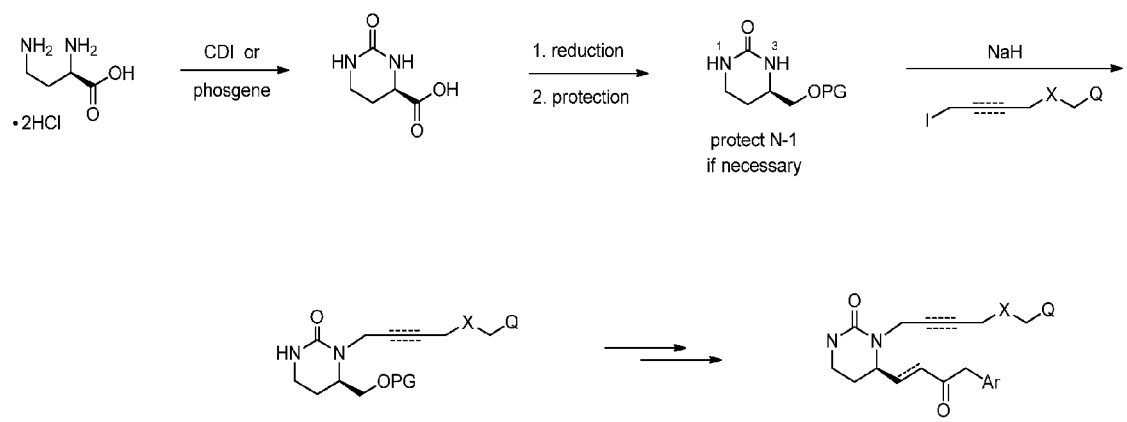

Alternatively, one might employ a method such as that shown in FIG. 5. Cyclization of readily available 2,4-diaminobutyric acid to the tetrahydro-pyrimidin-2-one core would be accomplished with phosgene or CDI as described in Cappecchi, et al. (*J. Org. Chem.* 1983, 48, 2014-2021) as follows:

"2,4-Diaminobutanoic acid dihydrochloride (1.91 g, 10 mmol) was dissolved in 400 mL of $H_2O$ and adjusted to pH 8.0. This pH was maintained (pH stat, 25% NaOH titrant) during the reaction. The solution was cooled in an ice bath, and 1,1-carbonyldiimidazole (CDI; 1.62 g, 1 equiv) in 25 mL of $CH_3CN$ was added slowly over a 20-min period (1.28 mmol of base consumed). The reaction was then stirred at room temperature for 7 h (an additional 4.38 mmol) of base consumed). The addition of 1 equiv of CDI was repeated after 24 h. After a 48-h total reaction time, the reaction mixture was applied to a 5.0×23 cm Bio-Rad AG 50W-X2 column (cation exchange) and eluted with water. The product 14 [2-Oxo-hexahydropyrimidine-4-carboxylic acid] was located by TLC and isolated by lyophilization of the appropriate fractions. The product was then purified by chromatography on a 2.5×18 cm DEAE-Sephadex column (gradient elution made from 0.75 L of $H_2O$ and 0.75 L of 0.5 M AcOH/pyridine, pH 3.9 buffer): yield 0.38 g (26%)."

Reduction and protection of the resulting alcohol would be followed by alkylation of N-3 to give the desired intermediate. Should alkylation occur preferably at N-1, then N-1 would be selectively protected (as its CBz, BOC or substituted benzyl derivative), then alkylation with the top chain precursor at N-3 should occur without incident. The methods of Billot and Young, or Saijo et al. or Old would then be used to elaborate the core molecule to the desired compounds.

Example 2

The biological activity of the compounds of Table 1 may be tested using the following procedures.

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors are washed with TME buffer, scraped from the bottom of the flasks, and homogenized for 30 sec using a Brinkman PT 10/35 polytron. TME buffer is added to achieve a final 40 ml volume in the centrifuge tubes (the composition of TME is 100 mM TRIS base, 20 mM $MgCl_2$, 2M EDTA; ION HCl is added to achieve a pH of 7.4).

The cell homogenate is centrifuged at 19000 r.p.m. for 20 min at 4° C. using a Beckman Ti-60 rotor. The resultant pellet is resuspended in TME buffer to give a final 1 mg/ml protein concentration, as determined by Biorad assay. Radioligand binding competition assays vs. [$^3$H-]17-phenyl $PGF_{2\alpha}$ (5 nM) are performed in a 100 µl volume for 60 min. Binding reactions are started by adding plasma membrane fraction. The reaction is terminated by the addition of 4 ml ice-cold TRIS-HCl buffer and rapid filtration through glass fiber GF/B filters using a Brandel cell harvester. The filters are washed 3 times with ice-cold buffer and oven dried for one hour.

[$^3$H-] $PGE_2$ (specific activity 180 Ci mmol) is used as the radioligand for EP receptors. [$^3$H] 17-phenyl $PGF_{2\alpha}$ is employed for FP receptor binding studies. Binding studies employing $EP_1$, $EP_2$, $EP_4$ and FP receptors are performed in duplicate in at least three separate experiments. A 200 µl assay volume is used. Incubations are for 60 min at 25° C. and are terminated by the addition of 4 ml of ice-cold 50 mM TRIS-HCl, followed by rapid filtration through Whatman GF/B filters and three additional 4 ml washes in a cell harvester (Brandel). Competition studies are performed using a final concentration of 5 nM [$^3$H]-$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293 (EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), are cultured in 100 mm culture dishes in high-glucose DMEM medium containing 10% fetal bovine serum, 2 mM 1-glutamine, 250 µg/ml geneticin (G418) and 200 µg/ml hygromycin B as selection markers, and 100 units/ml penicillin G, 100 µg/ml streptomycin and 0.25 µg/ml amphotericin B.

(b) Calcium Signal Studies on the FLIPR™

Cells are seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells are then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates are washed four times with HBSS-HEPES buffer to remove excess dye leaving 100 µl in each well. Plates are re-equilibrated to 37° C. for a few minutes.

Cells are excited with an Argon laser at 488 nm, and emission is measured through a 510-570 nm bandwidth emission filter (FLIPR™, Molecular Devices, Sunnyvale, Calif.). Drug solution is added in a 50 µl volume to each well to give the desired final concentration. The peak increase in fluorescence intensity is recorded for each well. On each plate, four wells each serve as negative (HBSS-HEPES buffer) and positive controls (standard agonists: BW245C (hDP); $PGE_2$ (h$EP_1$; h$EP_2$/Gqs5; h$EP_{3,4}$/Gqi5; h$EP_4$/Gqs5); $PGF_{2\alpha}$ (hFP); carbacyclin (hIP); U-46619 (hTP), depending on receptor). The peak fluorescence change in each drug-containing well is then expressed relative to the controls.

Compounds are tested in a high-throughput (HTS) or concentration-response (CoRe) format. In the HTS format, forty-four compounds per plate are examined in duplicates at a concentration of $10^{-5}$ M. To generate concentration-response curves, four compounds per plate are tested in duplicates in a concentration range between $10^{-5}$ and $10^{-11}$ M. The duplicate values are averaged. In either, HTS or CoRe format each compound is tested on at least 3 separate plates using cells from different passages to give an $n \geq 3$.

The results of these assays will demonstrate that the compounds disclosed herein have activity characteristic of prostaglandins, and will thus be useful in treating diseases such as glaucoma which are amenable to treatment by prostaglandins.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims

What is claimed is:
1. A compound comprising

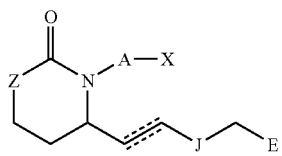

or a pharmaceutically acceptable salt thereof;
wherein a dashed line represents a double bond or a triple bond;
A is —$(CH_2)_6$—, cis —$CH_2CH=CH—(CH_2)_3$—, or —$CH_2C \equiv C—(CH_2)_3$—, wherein 1 or 2 carbon atoms may be substituted with S or O;
Z is NR, or NR;
X is selected from the group consisting of $CO_2H$, $CONHR_2$, $CONR_2$, $CON(OR)R$, $CON(CH_2CH_2OH)_2$, $CONH(CH_2CH_2OH)$, $CH_2OH$, $P(O)(OH)_2$, $CONHSO_2R$, $SO_2NR_2$, $SO_2HR$, and

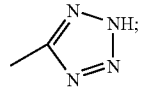

J is C=O or CHOH;
R is independently H, $C_1$-$C_6$ alkyl, phenyl, or biphenyl; and
E is $C_3$-$C_6$ alkyl, $C_4$-$C_{10}$ cycloalkyl, phenyl or napthyl having from 0 to 2 substituents, or a heteroaromatic moiety having from 0 to 2 substituents, wherein said substituents comprise up to 4 non-hydrogen atoms.

2. The compound of claim 1 having the formula

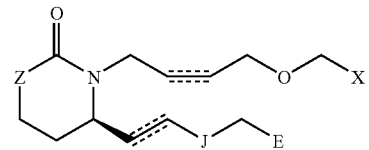

or a pharmaceutically acceptable salt thereof.

3. The compound of claim 1 having the formula

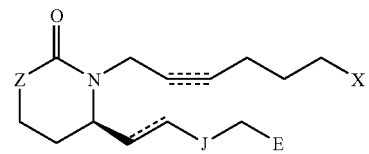

or a pharmaceutically acceptable salt thereof.

4. The compound of claim 3 wherein Z is NH.
5. The compound of claim 3 wherein J is C=O.
6. The compound of claim 3 wherein J is CHOH.
7. The compound of claim 3 wherein X is $CO_2H$.
8. The compound of claim 3 wherein E is phenyl, thienyl, furyl, pyridinyl, napthyl, benzothienyl, or benzofuryl having from 0 to 2 substituents comprising up to 4 non-hydrogen atoms.
9. The compound of claim 3 wherein E is n-butyl.
10. The compound of claim 1 having the formula

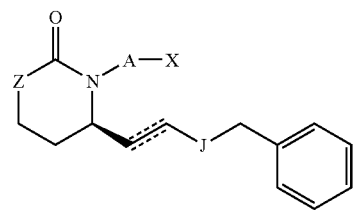

or a pharmaceutically acceptable salt thereof.

11. The compound of claim 1 having the formula

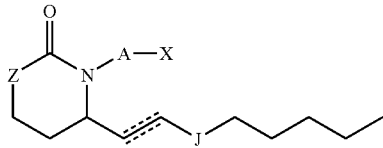

or a pharmaceutically acceptable salt or a prodrug thereof.

12. The compound of claim 1 having the formula

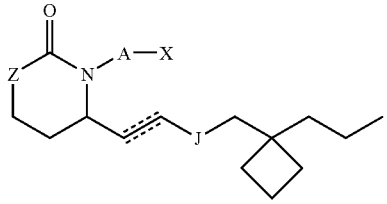

or a pharmaceutically acceptable salt thereof.

13. A liquid composition comprising a compound having the formula

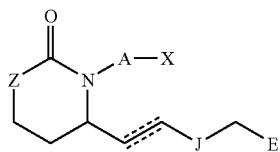

or a pharmaceutically acceptable salt thereof;
wherein a dashed line represents the presence or absence of a double bond or a triple bond;
A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O;
Z is NR, or NR;
X is selected from the group consisting of $CO_2H$, $CONHR_2$, $CONR_2$, $CON(OR)R$, $CON(CH_2CH_2OH)_2$, $CONH(CH_2CH_2OH)$, $CH_2OH$, $P(O)(OH)_2$, $CONHSO_2R$, $SO_2NR_2$, $SO_2NHR$, and

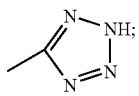

J is C=O or CHOH;
R is independently H, $C_1$-$C_6$ alkyl, phenyl, or biphenyl; and
E is $C_3$-$C_6$ alkyl, $C_4$-$C_{10}$ cycloalkyl, phenyl or napthyl having from 0 to 2 substituents, or a heteroaromatic moiety having from 0 to 2 substituents, wherein said substituents comprise up to 4 non-hydrogen atoms.

14. A method of treating glaucoma or ocular hypertension comprising administering a compound to a mammal, said compound having the formula

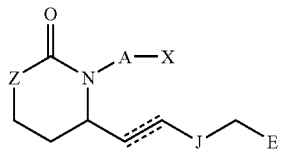

or a pharmaceutically acceptable salt thereof;
wherein a dashed line represents the presence or absence of a double bond or a triple bond;
A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O;
Z is NR, or NR;
X is selected from the group consisting of $CO_2H$, $CONHR_2$, $CONR_2$, $CON(OR)R$, $CON(CH_2CH_2OH)_2$, $CONH(CH_2CH_2OH)$, $CH_2OH$, $P(O)(OH)_2$, $CONHSO_2R$, $SO_2NR_2$, $SO_2NHR$, and

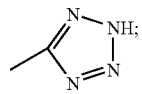

J is C=O or CHOH;
R is independently H, $C_1$-$C_6$ alkyl, phenyl, or biphenyl; and
E is $C_3$-$C_6$ alkyl, $C_4$-$C_{10}$ cycloalkyl, phenyl or napthyl having from 0 to 2 substituents, or a heteroaromatic moiety having from 0 to 2 substituents, wherein said substituents comprise up to 4 non-hydrogen atoms.

* * * * *

UNITED STATES PATENT AND TRADEMARK OFFICE
CERTIFICATE OF CORRECTION

PATENT NO. : 7,705,008 B2  Page 1 of 2
APPLICATION NO. : 12/191779
DATED : April 27, 2010
INVENTOR(S) : David W. Old et al.

It is certified that error appears in the above-identified patent and that said Letters Patent is hereby corrected as shown below:

In column 2, line 43, delete "Opthalmol." and insert -- Ophthalmol. --, therefor.

In column 2, line 51, delete "Opthalmol." and insert -- Ophthalmol. --, therefor.

In column 3, line 47, delete "napthyl" and insert -- naphthyl --, therefor.

In column 4, line 13, after "useful" insert -- . --.

In column 5, line 10, delete "  " and insert

-- 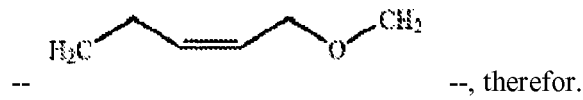 --, therefor.

In column 6, line 61, delete "napthyl" and insert -- naphthyl --, therefor.

In column 6, line 66, delete "penyl," and insert -- pentyl, --, therefor.

In column 7, line 51, delete "moeity" and insert -- moiety --, therefor.

In column 20, line 6, delete "Scheme 1" and insert -- FIG. 1 --, therefor.

Figure 4:
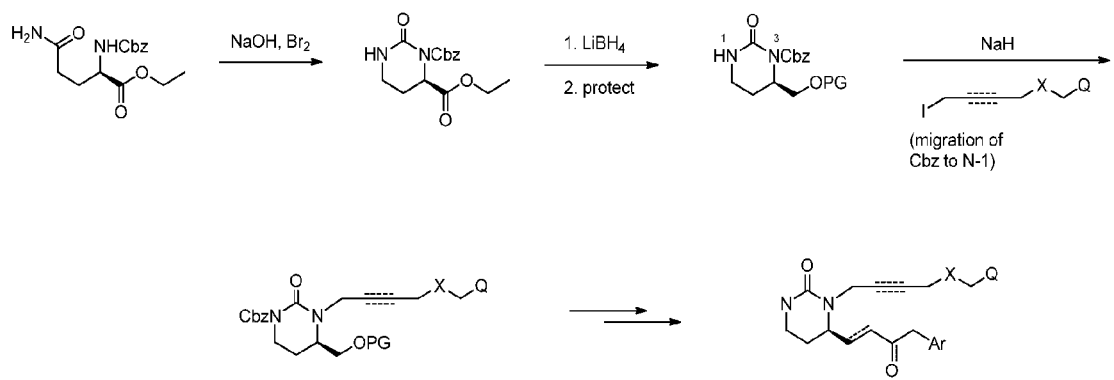

In column 21, line 24, delete "Scheme 4" and insert -- FIG. 4 --, therefor.

In column 23, line 47, after "claims" insert -- . --.

In column 23, line 65, in Claim 1, after "is" delete "NR, or".

In column 24, line 2, in Claim 1, delete "SO₂HR," and insert -- SO₂NHR, --, therefor.

In column 24, line 13, in Claim 1, delete "napthyl" and insert -- naphthyl --, therefor.

In column 24, line 50, in Claim 8, delete "napthyl," and insert -- naphthyl, --, therefor.

In column 25, line 12, in Claim 11, after "salt" delete "or a prodrug".

In column 25 line 45, in Claim 13, after "is" delete "NR, or".

Signed and Sealed this

Twenty-third Day of November, 2010

David J. Kappos
*Director of the United States Patent and Trademark Office*

CERTIFICATE OF CORRECTION (continued)
U.S. Pat. No. 7,705,008 B2

In column 26, line 10, in Claim 13, delete "napthyl" and insert -- naphthyl --, therefor.

In column 26, line 32, in Claim 14, after "is" delete "NR, or".

In column 26, line 46, in Claim 14, delete "napthyl" and insert -- naphthyl --, therefor.